United States Patent [19]

Stephen et al.

[11] 4,405,305

[45] Sep. 20, 1983

[54] SUBCUTANEOUS PERITONEAL INJECTION CATHETER

[75] Inventors: Robert L. Stephen; Carl Kablitz; Barry K. Hanover; Stephen C. Jacobsen; Jeffrey J. Harrow, all of Salt Lake City, Utah

[73] Assignee: University of Utah Research Foundation, Salt Lake City, Utah

[21] Appl. No.: 235,185

[22] Filed: Feb. 17, 1981

Related U.S. Application Data

[63] Continuation-in-part of Ser. No. 200,830, Oct. 27, 1980.

[51] Int. Cl.³ ............................................. A61M 25/00
[52] U.S. Cl. ....................................... 604/49; 604/29; 604/175
[58] Field of Search .............. 128/214 R, 274, 213 A, 128/348–350; 604/28, 29, 49, 175, 8–10

[56] References Cited

U.S. PATENT DOCUMENTS

| | | | |
|---|---|---|---|
| 3,137,299 | 6/1964 | Tabor | 128/207.16 |
| 3,310,051 | 3/1967 | Schulte | 128/350 R |
| 3,783,868 | 1/1974 | Bokros | 128/260 |
| 3,818,511 | 6/1974 | Goldberg et al. | 128/348 X |
| 4,184,497 | 1/1980 | Kolff et al. | 128/213 A |
| 4,256,102 | 3/1981 | Monaco | 128/213 A |

OTHER PUBLICATIONS

Boen et al.–Trans. Amer. Soc. Artificial Inter. Orgs., vol. VIII, 1962, pp. 256–262.

Primary Examiner—Dalton L. Truluck
Attorney, Agent, or Firm—H. Ross Workman; Allen R. Jensen; Berne S. Broadbent

[57] ABSTRACT

A novel implantable, peritoneal injection catheter apparatus and method, the apparatus including an open top, fluid-receiving reservoir mounted to one end of a hollow stem and a penetrable membrane covering the open top of the receiving reservoir. The hollow stem is configurated to extend into the peritoneal cavity and includes a retaining flange system for retaining the hollow stem in fluid communication with the peritoneal cavity. The penetrable membrane serves as an injection site for inserting a hollow needle into the receiving reservoir. The penetrable membrane also includes a dome configuration that may be depressed to expel injection fluids from the reservoir into the peritoneal cavity. A substantial portion of the injection catheter is covered with a velour coating to accomodate tissue ingrowth for further securement of the catheter in the tissue of the abdominal wall.

33 Claims, 6 Drawing Figures

SUBCUTANEOUS PERITONEAL INJECTION CATHETER

RELATED APPLICATIONS

This application is a continuation-in-part application of our copending application Ser. No. 200,830 filed Oct. 27, 1980 for SUBCUTANEOUS PERITONEAL INJECTION CATHETER.

BACKGROUND

1. Field of the Invention

This invention relates to injection catheters and, more particularly, to a novel subcutaneous peritoneal injection catheter apparatus and method for providing injection access to the peritoneal cavity.

2. The Prior Art

Glucose is a major fuel for the body with the brain being the notable consumer. Insulin is required by many, but not all, tissues for the uptake and/or utilization of glucose.

The liver and pancreas are the pivotal organs in glucose control with insulin serving as a vital regulatory hormone. For example, in response to rising levels of glucose, the pancreatic beta cells secrete insulin which travels from the pancreas to the portal vein and then to the liver where the liver extracts approximately 50 percent of the insulin. The remaining 50% of the insulin then travels throughout the rest of the body to specific receptors in other tissues. In response to insulin, the liver commences storage of glucose in the form of glycogen (a starch). In the fasting state, the liver releases a steady output of this stored glucose thereby supplying many body tissues with their requisite amounts of glucose.

Conversely glucose utilization by other tissues is insignificantly affected by normal pancreatic insulin secretion. It has been stated that the greater response of the liver as compared to peripheral tissues (fat and muscle) to small changes in insulin levels need not reflect an inherently greater sensitivity on the part of the liver cell (hepatocyte), rather, it may be a consequence of high ambient levels of endogenous (self-produced) insulin in portal as compared to peripheral blood. In summary, therefore, the major effect of insulin in a normal human is to lower the blood glucose levels by decreasing the rate of glucose output by the liver.

Diabetics suffer from relative or absolute deficiency in insulin secretion (resulting in high blood sugar levels) and tissue cells which are "starving" for glucose yet are unable to "feed" (absorb glucose) in the absence of insulin. Historically, the treatment has been to provide insulin by injections into the peripheral circulation either from a subcutaneous depot or as an intravenous slow infusion. The result is that only about 10 percent of the administered dose of insulin reaches the liver as compared to approximately 50 percent in normal persons. As a consequence, hepatic glucose production is not first reduced; rather, blood glucose is lowered by increased utilization by other tissues (muscle, fat) as a result of the presence of high levels of insulin in the peripheral circulation. Accordingly, normal levels of blood sugar are achieved only by carefully matching any increased peripheral utilization of blood sugar to an increased hepatic production, which is inherently much more difficult than simply decreasing hepatic glucose production.

When demand for blood sugar exceeds the supply (as a result of too much insulin injected), the blood glucose drops below normal values. There is little glucose reserve since the liver, in its state of under-insulinization, is already releasing glucose. The result is that the blood sugar level will plummet despite adequate levels of counterregulatory hormones (glucagon, epinephine, norepinephine, and growth hormone) whose actions are to increase liver production of glucose in emergency situations. This hypoglycemic reaction, a progression of symptoms from nervousness, sweating, stupor, unconsciousness, and occasionally, irreparable brain damage, will occur until sugary substances are taken by mouth or intravenously.

The ongoing cycle between hyperglycemia and hypoglycemia has created a basic rift in the philosophy of diabetic control. The "tight control" philosophy claims that the long-term devastations of diabetes (blindness, heart attacks, kidney failure, and loss of extremities) are due to abnormally elevated sugar levels, and strives to keep blood sugar within the normal range even at the risk of frequent (more than once a week) hypoglycemic reactions. The converse of the foregoing is the "loose control" philosophy which is based on the presumption that the basic foundation of the tight control philosophy has yet to be proved and that the considerable risks of hypoglycemic reactions are not worth an unproved benefit.

The intraperitoneal delivery of insulin has recently been investigated as an alternative to both the intravenous and subcutaneous delivery sites. Although access to the intraperitoneal site is more difficult, it has the potential advantages of avoiding peripheral hyperinsulinaemia (high blood insulin levels), insulinizing the liver via direct portal venous system insulin absorption, and more rapid absorption than subcutaneously delivered insulin. Preliminary results appear favorable for intraperitoneal delivery of insulin.

Insulin delivery into the peritoneum is reported to have resulted in a rapid rise in circulating peripheral insulin concentration, which peaked at 30-45 minutes following the initiation of insulin delivery. Furthermore, when the infusion rate of intraperitoneal insulin was reduced to the background rate, a gradual decline in peripheral insulin concentration to normal fasting values resulted. (This free insulin response contrasted to the continuing high levels following subcutaneous insulin injection.) It was, therefore, concluded that normalization of plasma insulin profiles was achievable with intraperitoneal infusion of insulin and, further, that meal-related hyperglycemia (elevated blood glucose) is well-controlled with intraperitoneal insulin and yet hypoglycemic episodes are reduced compared to subcutaneous delivery. For reference, see "Normalization of Plasma Insulin Profiles With Intraperitoneal Insulin Infusion in Diabetic Man," D. S. Schade, R. P. Eaton, N. M. Friedman, and W. J. Spencer, *DIABETOLOGIA*, 19, 35-39 (1980).

The peritoneum is the largest serous membrane in the body and consists, in the male, of a closed sac, a part of which is applied against the abdominal parietes, while the remainder is reflected over the contained viscera. In the female, the peritoneum is not a closed sac, since the free ends of the uterine tubes open directly into the peritoneal cavity. The part which lines the abdominal wall is named the parietal peritoneum and that which is reflected over the contained viscera constitutes the visceral peritoneum. The space between the parietal and visceral layers of the peritoneum is named the peritoneal cavity. However, under normal conditions, this cavity is merely a potential one, since the parietal and visceral layers are in contact.

For a number of years, it has been well-known that the peritoneal membrane will function fairly effectively as an exchange membrane for various substances. As early as 1923, peritoneal dialysis (an artificial kidney format) was first applied clinically. The first peritoneal access device was a piece of rubber tubing temporarily sutured in place. In 1960, peritoneal dialysis was becoming an established form of artificial kidney therapy and, in order to lessen the discomfort of repeated, temporary punctures into the peritoneal cavity, various access devices permitting the painless insertion of the acute or temporary peritoneal catheters were developed.

The most common peritoneal access device is of the Tenckhoff type: a capped percutaneous (through the skin) silastic tube passes through the abdominal wall into the peritoneal cavity.

Another peritoneal access device (the "Gottloib" prosthesis) consists of a short, "golf tee" design that is adapted to be placed under the skin with a hollow tubular portion extending just into the peritoneal cavity. This device is designed specifically to allow the insertion of an acute peritoneal catheter (a Trocath) through the skin and down through this access tubing directly into the peritoneal cavity. Another device consists of a catheter buried underneath the skin and extending into the peritoneal cavity via a long tubing. Peritoneal dialysis is performed by inserting a large needle into the subcutaneous portion of the catheter.

All of the devices known were designed with one purpose in view: peritoneal dialysis, and are used almost exclusively by one group of patients, those with End-Stage Renal Disease (ESRD), whose kidney function will never return. In simple terms, therefore, the access devices to the peritoneal cavity plus the peritoneal cavity itself constitute an artificial kidney.

A variety of drugs or other fluids are frequently added to the large volumes of peritoneal dialysis solutions and are thus instilled (injected) into the peritoneal cavity for various therapeutic reasons. Some examples of these drugs are antibiotics, amino acids, and insulin (for diabetics). However, such therapeutic maneuvers are fortuitous in that the clinician is simply taking advantage of a particular situation, that is, a peritoneal access device emplaced in a particular group of patients.

In spite of the foregoing, there are cogent reasons for not using existing, permanent peritoneal accesss devices for simple drug injections in a wide variety of patients not suffering ESRD. Most of these devices have what might be termed a relatively large internal volume, that is, it would require anywhere between about five and twenty milliliters, (depending upon the device), to fill the device with fluid. This volume which is a dead volume or dead space, is a very real hindrance in that the injected fluid may simply remain within the device itself instead of entering the peritoneal cavity.

In view of the foregoing, it would be an advancement in the art to provide a novel subcutaneous peritoneal injection catheter which may be readily implanted underneath the skin and provide direct access into the peritoneal cavity. It would also be an advancement in the art to provide a subcutaneous peritoneal injection catheter having a relatively small internal volume while providing a relatively enlarged target area. Such a novel subcutaneous peritoneal injection catheter apparatus and method is disclosed and claimed herein.

BRIEF SUMMARY AND OBJECTS OF THE INVENTION

The present invention relates to a novel subcutaneous peritoneal injection catheter apparatus and method, the apparatus including a receiving chamber or reservoir having a relatively small internal volume while employing a penetrable membrane as relatively enlarged target surface area. The reservoir is interconnected with the peritoneal cavity by a hollow stem. The penetrable membrane accomodates a hollow needle being inserted into the receiving reservoir and is configurated with a dome-like profile so that the membrane may also be depressed to expel insulin from the receiving reservoir into the peritoneal cavity. Portions of the catheter are covered with a velour surface to accomodate tissue ingrowth and securement of the catheter subcutaneously.

It is, therefore, a primary object of this invention to provide improvements in implantable injection catheters.

Another object of this invention is to provide an improved method for injecting fluids into the peritoneal cavity.

Another object of this invention is to provide a novel subcutaneous peritoneal injection catheter having a relatively small fluid capacity while presenting a relatively large target surface area.

Another object of this invention is to provide a novel peritoneal catheter having a receiving reservoir and a dome-like cover for the receiving reservoir, the dome-like cover serving as an expulsion membrane for forcing fluids from the receiving reservoir into the peritoneal cavity.

Another object of this invention is to provide an implantable injection catheter having securement means for securing the catheter subcutaneously.

These and other objects and features of the present invention will become more fully apparent from the following description and appended claims taken in conjunction with the accompanying drawing.

DETAILED DESCRIPTION OF THE PREFERRED EMBODIMENTS

Figure 1:
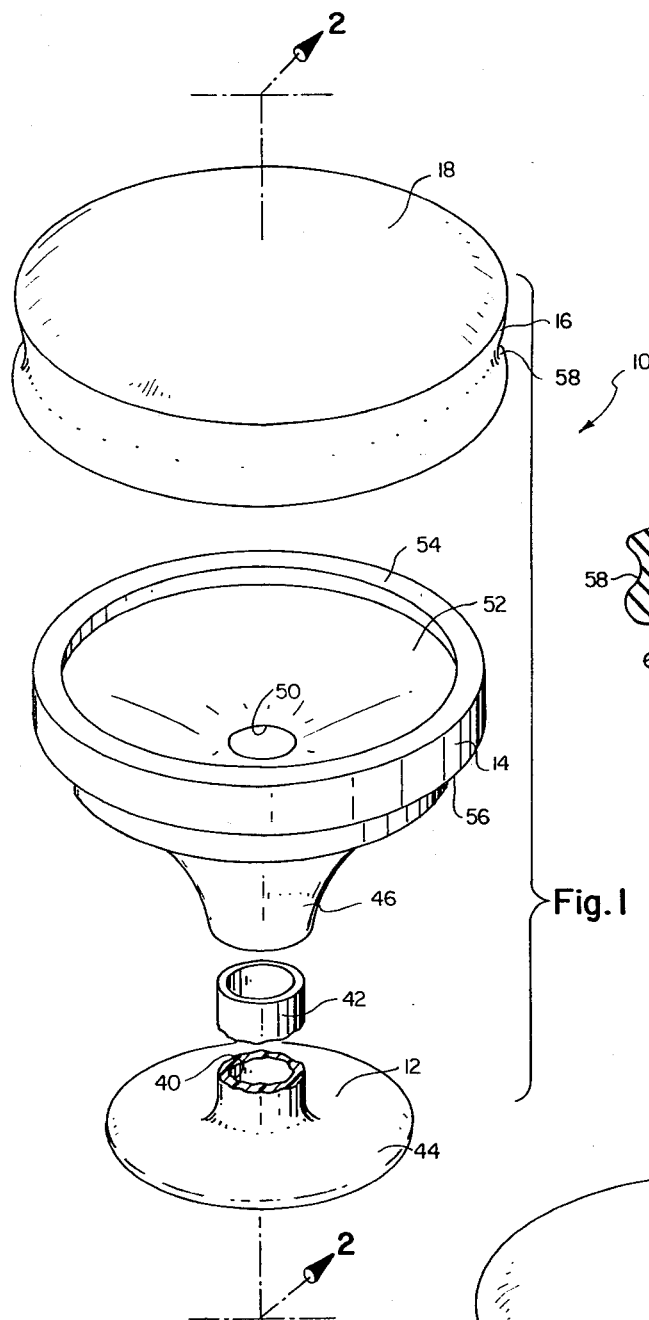
FIG. 1 is an exploded, perspective view of the stem, body and cover that provide the basic structure of the novel peritoneal catheter of this invention.

The invention is best understood by reference to the drawing wherein like parts are designated with like numerals throughout.

GENERAL DISCUSSION

As a general restatement, diabetes is generally identified as a metabolic disorder in which the ability to metabolize carbohydrates and, more particularly, glucose, is more or less completely lost due to faulty pancreatic activity and consequent disturbance of normal insulin mechanism. Insulin acts by regulating the metabolism of glucose, and there is evidence that it does this by facilitating the transport of glucose through the cell membrane. A corollary hormone, glucagon, acts by stimulating the conversion of glycogen into glucose by activating liver phosphorylase. The subsequent release of glucose into the bloodstream causes a hyperglycemic effect which is thus opposite to the hypoglycemic, or blood-sugar-lowering effect, of insulin. It appears that there is a natural balance of action of the two hormones resulting in the control of glucose release and utilization. Insulin is secreted by certain cells of a pancreatic tissue known as the Islets of Langerhans. A deficiency of these cells and consequent decrease in insulin secretion has been found in human subjects who developed diabetes at a relatively young age. Such patients usually suffer an almost total lack of insulin and are designated as "juvenile onset diabetics" or "ketosis-prone diabetics." Such patients die if not treated by insulin injections.

Routine administration of insulin used to treat patients with ketosis-prone diabetics leaves much to be desired. Once or twice daily injections with any of the long-acting insulins, although continuous in a basal sense, makes no pretense at supplying controlled variable amounts of insulin consequent upon changing metabolic demands. Furtheremore, aggressive peripheral insulin administration (that is, insulin injected subcutaneously, intramuscularly or intravenously), used in an attempt to obtain tight control of glycemia, may lead to periods of sustained hyperglycemia that occasionally cycles into a hypoglycemic state. It is possible that changes in circulating, metabolically active hormones and/or receptor site concentrations are responsible for this situation.

Possibly the major problem encountered in controlling glycemia is the unphysiological administrative route of therapeutic insulin. The liver, the prime organ involved in regulation of blood glucose levels, is initially bypassed following injection by the peripheral route (subcutaneous, intramuscular, intravenous). Achieving normoglycemia by injection of peripheral insulin inevitably engenders high blood insulin levels (hyperinsulinemia). The physiological insult imposed by hyperinsulinemia perturbs many metabolic feedback loop controls, which in turn lowers the gain of this web of servo mechanisms. The end result is that good, sustained control of glycemia is achieved at the expense of a razor-thin margin between normoglycemia and hypoglycemia. Prolonged hypoglycemia kills people, so diabetologists over the years have generally followed safety-first rules: allow the patient to function in a controlled hyperglycemic state. However, the evidence is now tilting towards a prolonged, if controlled, hyperglycemic state as being at least part of a general metabolic derangement, which causes longterm accelerated vascular and peripheral nerve pathology.

In an effort to regulate these undesirable alternatives (hyperglycemia⇌hypoglycemia), various closed and open loop control delivery systems have been developed. Yet the therapists involved still persist in using these systems to deliver insulin peripherally. Closed loop delivery systems are synonymous with prolonged hospitalization: open loop delivery systems actually produce a more sustained, if somewhat better regulated, hyperinsulinemic state. Additionally, they are awkward to wear, they require tubing sets and implanted needles and, in spite of claims made to the contrary, they can malfunction ("surge"), usually at the most inconvenient hours.

Portal venous administration of insulin has given highly encouraging results in experimental animals: less insulin is required to achieve normoglycemia and hyperinsulinemia is avoided. However, long-term access directly into the portal system carries several severe risks all of which are lethal. Nevertheless, there is a secondary and much safer route leading directly into the portal system: the visceral (that covering most of the gut) peritoneal membrane.

Intraperitoneal Insulin. Intraperitoneal delivery of insulin has been performed in ketosis-prone diabetic human subjects on a short-term (hours) basis, achieving comparable glycemic control to that achieved with subcutaneous insulin, yet with only approximately half the integrated blood levels of plasma insulin. Intraperitoneal insulin has also been utilized long term in patients with ketosisprone diabetes and end-stage renal disease treated by continuous ambulatory peritoneal dialysis. (An artificial kidney format). Adequate control was achieved in the three patients reported.

There is no readily available documentation substantiating the thesis that the intraperitoneal delivery of drugs is primarily absorbed into the portal venous system (visceral peritoneum) rather than the general systemic venous system (parietal peritoneum). However, there is a considerable amount of indirect evidence for this hypothesis: (1) at laparotomy one's field of vision is virtually totally obscured by mesenteric (visceral) peritoneum; (2) the work of other researchers indicates that control of glycemia by intraperitoneal insulin is good yet there was a 50% "loss"—presumably picked up by the liver before reaching the peripheral circulation; (3) intraperitoneal administration of sodium nitroprusside (for the purpose of causing intraperitoneal vasodilatation) resulted in no detectable levels of peripheral plasma thiocyanate: it is assumed that metabolism of nitroprusside by the liver accounted for the lack of peripheral thiocyanate. One researcher stated that he had always presumed intraperitoneal administration of drugs resulted in their direct transfer to the portal venous system but had never tested the hypothesis directly nor could he think of anyone else who had done so.

One final point must be made: Intraperitoneal administration of various dialysis fluids and certain drugs such as antibiotics, permanent access to the peritoneal cavity and knowledge of the physiological migratory route of insulin have been with us for many years. Therefore, why has not intraperitoneal delivery of insulin been utilized in the past? In fact, this route has been used in patients who are diabetic and suffering end-stage renal disease (ESRD). However, until recently, chronic peritoneal dialysis was performed on an intermittent basis (once, twice or thrice weekly), which encouraged only widely spaced use of intraperitoneal insulin. Also, peritoneal dialysate was supplied in glass bottles and insulin sticks to glass in quite substantial amounts. Finally, until recently there were very few diabetic patients treated for ESRD.

The major impediment to utilizing the intraperitoneal route for delivery of insulin in patients not suffering ESRD is lack of a suitable intraperitoneal access device. The majority of standard peritoneal catheters are long, clumsy, percutaneous, infection-prone silastic tubes. One balks at the thought of any patient wearing one of these unless absolutely necessary.

The present invention is a peritoneal access device with the following constraints. (1) The dead space or dead volume of the device is minimal. (2) It presents a large surface area (consistent with the first constraint) to allow for injection of various drugs. (3) It is designed purely and simply for one-way flow, i.e., drug injection is inward only; there is no outflow considered. (4) It is designed so that a variety of drugs may be injected into the peritoneal cavity. (5) It has a resilient, dome surface above the receiving reservoir so that the dome may be depressed to expel insulin from the receiving reservoir into the peritoneal cavity. (6) It is not designed for peritoneal dialysis and, in fact, would not function if used for this purpose.

The Preferred Embodiment

Figure 2:
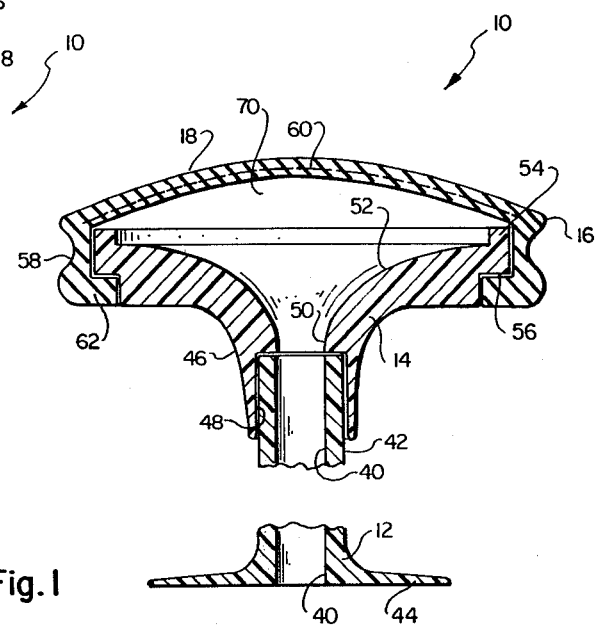
FIG. 2 is a cross-sectional view taken along lines 2—2 of FIG. 1.
Figure 4:
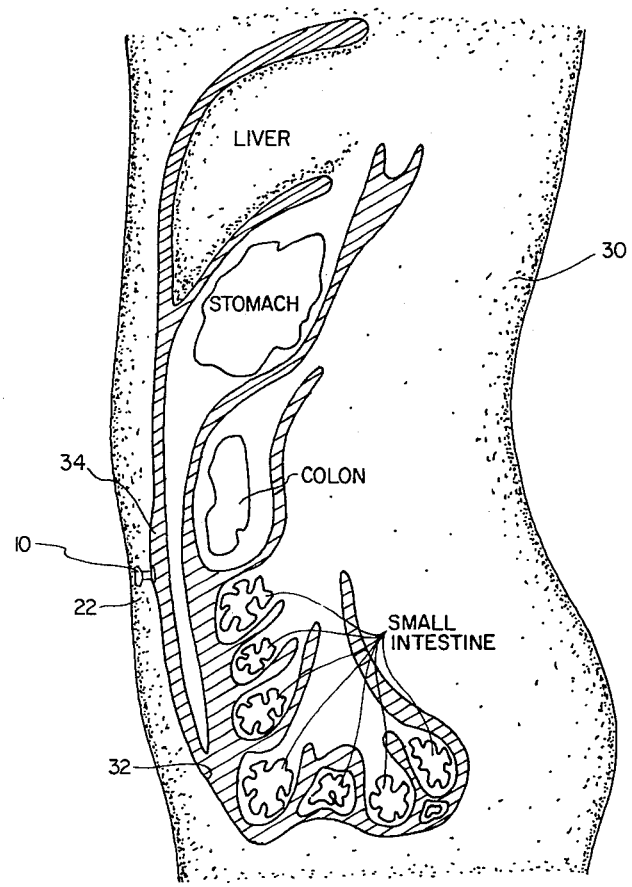
FIG. 4 is a schematic illustration of the novel peritoneal catheter of this invention shown implanted in the abdominal wall of a torso.
Figure 5:
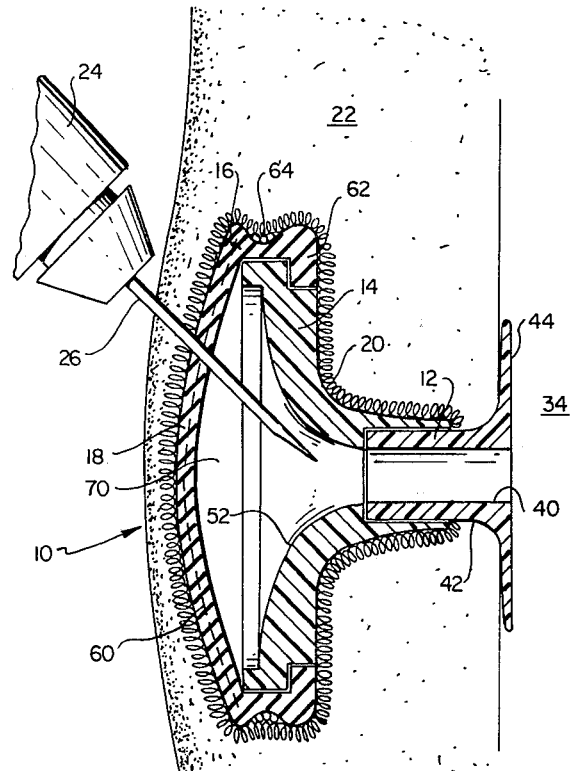
FIG. 5 is a cross-sectional, schematic illustration of the novel peritoneal catheter of this invention implanted in the abdominal wall and shown in cooperation with a hypodermic syringe.
Figure 6:
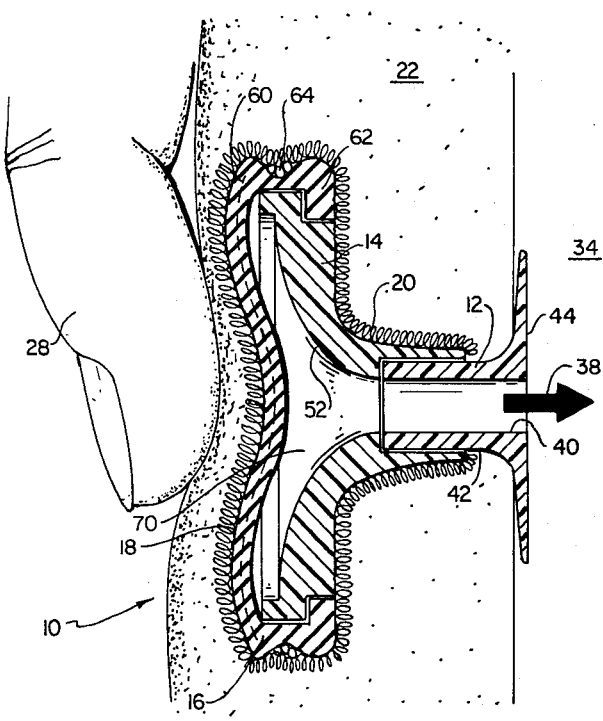
FIG. 6 is a cross-sectional, schematic illustration of the novel peritoneal catheter of this invention implanted in the abdominal wall and being compressed to expel fluids therefrom into the peritoneal cavity.

Referring now more particularly to FIGS. 1 and 2, the peritoneal catheter apparatus of this invention is shown generally at 10 and includes a stem 12, a body 14, and a cap 16. Stem 12 is configured as a hollow, tubular column 42 having a diametrally enlarged base 44 at one end and a hollow lumen 40 extending therethrough. Column 42 is shown broken in FIGS. 1 and 2 to demonstrate that its length is adjustable. Importantly, it is possible to selectively predetermine the length of column 42 and thereby adapt peritoneal catheter 10 for implantation in an abdominal wall 22 (FIGS. 4-6) having any suitable thickness as will be discussed more fully hereinafter. Base 44 is formed as a diametrally enlarged flange that serves as a retention member to inhibit peritoneal stem 12 from being completely withdrawn into the tissue of abdominal wall 22 with a corresponding loss of fluid communication through lumen 40 into peritoneal cavity 34 (FIGS. 4-6).

Body 14 serves as the basal member for peritoneal catheter 10 and is configured with a funnel-like section 52 having a relatively shallow depth in comparison with the relatively enlarged diameter. The depth of funnel section 52 is selectively predetermined so as to contain a predetermined body of insulin which may be suitably retained momentarily or expelled, as desired, as will be set forth more fully hereinafter. Funnel section 52 is surrounded at its upper edge by an upstanding rim 54 and terminates downwardly toward its center in a throat 50. Body 14 is fabricated from a suitable, puncture-resistant plastic material such as a conventional, biocompatible polyurethane. Body 14 is also provided with sufficient thickness so as to preclude inadvertent puncture by a needle 26 (FIG. 5) as will be set forth more fully hereinafter.

The opposite edge of rim 54 is formed as a retainer shelf 56 for the purpose of retaining an edge or lip 62 of cap 16. The lower portion of body 14 includes a neck 46 having a coaxial counterbore 48. The internal diameter of counterbore 48 is selectively predetermined so that column 42 may be telescopically received into abutment with throat 50. The diameter of throat 50 matches that of lumen 40 to provide a continuous, smooth flow channel through peritoneal catheter 10.

The height of rim 54, diameter and depth of funnel section 52 in combination with the hemispherical radius of cap 16 selectively predetermines the volume of the resulting, receiving reservoir 70. For example, one presently preferred embodiment of peritoneal catheter 10 had an internal volume of about 3.67 milliliters in combination with a maximum external diameter of 41 millimeters and a height of about 25 millimeters. Clearly, of course, the volume of receiving reservoir 70 varies somewhat with height since the length of column 42 is adjustable as set forth hereinbefore.

Figure 3:
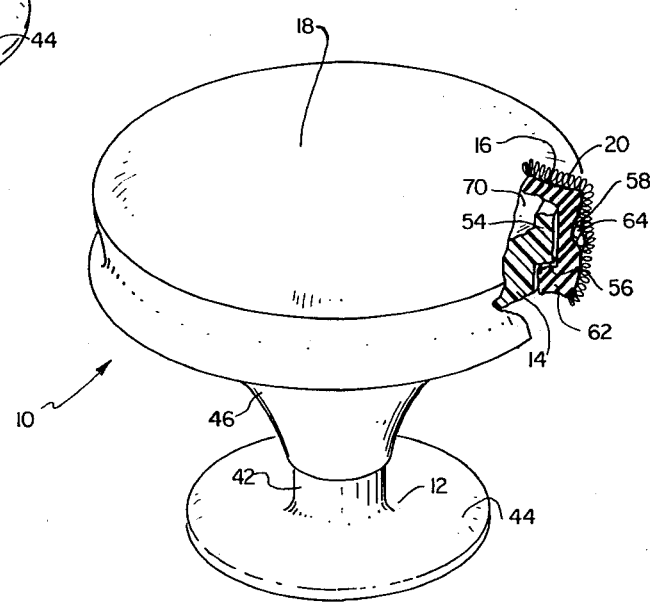
FIG. 3 is a perspective view of the novel peritoneal catheter of this invention with portions broken away to reveal internal construction.

Cap 16 is configured with an outwardly curved, dome-like puncture zone shown as dome 18 and is fabricated from a suitable, silicone rubber material having a reinforcing 60 embedded therein. The outer circumference of cap 16 includes an inwardly directed, circumferential lip 62 adapted to be received in snap-fit relationship with shelf 56 for the purpose of mounting cap 16 to body 14. A suture-receiving channel is formed as a circumferential groove 58 for the purpose of further securing cap 16 to body 14 with a suture 64 (FIGS. 3, 5 and 6). Cap 16 is fabricated from a suitable biocompatible material such as silicone rubber having the desired characteristics of being (a) resilient, (b) readily penetrable and (c) resealable to accomodate being flexed and punctured numerous times without degradation of the structural integrity of cap 60.

Referring now more particularly to FIG. 3, peritoneal catheter 10 and, more particularly, cap 16 and body 14 (FIGS. 1 and 2) as well as a portion of column 42 is encapsulated in a suitable, biocompatible velour material 20 to accomodate tissue ingrowth with velour 20. One suitable material for velour 20 is a commercially available Dacron velour material. With particular reference to the cutout portion, a suitable, nonabsorbable suture 64 is tightly wrapped around the periphery of cap 16 in groove 58. Suture 64 thereby provides additional securement for retaining cap 16 on body 14. This is particularly useful since forces directed inwardly against cap 16 result in corresponding radial forces tending to dislodge lip 62 from shelf 56. Thus, sutures 64 provide an additional safety feature for peritoneal catheter 10.

Referring now more particularly to FIG. 4, peritoneal catheter 10 is shown implanted in abdominal wall 22 of a torso 30 and provides fluid communication from peritoneal catheter 10 with the peritoneal membrane 32 surrounding peritoneal cavity 34. It should be noted that peritoneal cavity 34 is shown somewhat distended as though infused with dialysate in order to more clearly set forth the environment of peritoneal catheter 10. Advantageously, peritoneal catheter 10 is readily accessible via a conventional hypodermic syringe as will be discussed more fully hereinafter.

Referring now more particularly to FIGS. 5 and 6, peritoneal catheter 10 is shown as implanted in abdominal wall 22. Importantly, the diametrally enlarged base 44 precludes inadvertent retraction of catheter 10 into abdominal wall 22 thereby retaining lumen 40 in an open configuration and in fluid communication between reception reservoir 70 and peritoneal cavity 34. Additionally, tissue ingrowth is provided through the covering of a major portion of peritoneal catheter 10 with the velour covering 20.

In operation, the user (not shown) injects insulin into reservoir 70 by pentrating the relatively enlarged, dome 18 with a conventional, hollow needle 26 on the end of a syringe 24. Advantageously, the insulin in reservoir 70 may be allowed to slowly percolate through lumen 40 into peritoneal cavity 34 or, upon demand, the user (not shown) may depress dome 18 with a finger 28 (FIG. 6) forceably expelling insulin from reservoir 70 through lumen 40 as shown schematically at arrow 38.

The contour of funnel section 52 is selectively preconfigured so as to accomodate dome 18 being depressed inwardly to a contour generally corresponding to the contour of funnel section 52. It is therefore possible for substantially all of the fluid in reservoir 70 to be readily expelled therefrom. The resiliency of dome 18 returns cap 16 to its original configuration creating a partial vacuum in reservoir 70 so that a portion of fluid in peritoneal cavity 34 is drawn therein. Repeat depression of dome 18 causes the fluid of peritoneal cavity 34 to completely flush reservoir 70.

Experimentally, a radiopaque dye was injected into a peritoneal catheter 10 implanted in an abdominal wall 22. X-ray examination revealed a trickle of dye into peritoneal cavity 34 immediately after injection. Compression of dome 18 caused a surge of dye to be discharged into peritoneal cavity 34. All dye was flushed from reservoir 70 within three compression and release cycles of dome 18. This means that insulin may be injected into reservoir 70 where it will be readily available for slow release into peritoneal cavity 34 or may be rapidly expelled as required. It is, therefore, clearly possible for a patient to more closely monitor and control insulin delivery in a manner that will allow the liver to participate in the regulation of glucose release into the systemic circulation.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A subcutaneous conduit for injecting a drug into a peritoneal cavity, comprising:
    an injection receiver having a diametrally enlarged, convergent receiving surface and an opening in the receiving surface;
    a diametrally enlarged, penetrable cover across the receiving surface in spaced relationship therewith, the cover forming a receiving reservoir in combination with the receiving surface;
    a hollow stem having a proximal end and a distal end, the proximal end of the stem being attached to the injection receiver such that the stem forms a passageway extending from the opening in the receiving surface, the stem having a length sufficient that the stem penetrates the parietal peritoneal membrane and extends into the peritoneal cavity; and
    a diametrally enlarged flange attached to the stem such that, when the conduit is implanted under a layer of skin adjacent the peritoneal cavity and the flange is secured adjacent the parietal peritoneal membrane, the distal end of the hollow stem is directed toward the mesenteric peritoneal membrane.

2. A subcutaneous conduit as defined in claim 1 wherein the injection receiver comprises a penetration-resistant material.

3. A subcutaneous conduit as defined in claim 1 wherein the injection receiver comprises a generally circular periphery around the convergent receiving surface and a raised rim circumscribing the periphery, the rim assisting the cover in defining the receiving reservoir.

4. A subcutaneous conduit as defined in claim 3 wherein the injection receiver further comprises an annular shelf below the rim and the cover comprises an annular lip that is engagedly received by the shelf.

5. A subcutaneous conduit as defined in claim 1 wherein the diametrally enlarged flange is attached adjacent the distal end of the hollow stem, the flange thereby inhibiting the stem from retracting into tissue into which the conduit is implanted.

6. A subcutaneous conduit as defined in claim 1 wherein the injection receiver includes a bore which is countersunk into the receiver from the side opposite the convergent surface, the countersunk bore receiving the hollow stem with the passageway in alignment with the opening.

7. A subcutaneous conduit as defined in claim 1 wherein the penetrable cover is fabricated from a resilient material and with a dome-like configuration, the dome extending away from the receiving surface.

8. A subcutaneous conduit as defined in claim 1 wherein the cover comprises a circumferential groove, the groove serving a a channel for receiving a suture means, the suture means securing the cover to the injection receiver.

9. A subcutaneous conduit as defined in claim 1 wherein the conduit comprises a velour covering over at least a portion of the external surface of the conduit, the velour covering comprising a biocompatible material and providing for tissue ingrowth into the velour material.

10. A subcutaneously implantable injection conduit for injecting a drug into a peritoneal cavity, comprising:
    a hollow receptacle for receiving the drug, the hollow receptacle being formed as an open-top chamber;
    a penetrable membrane over the open top of the chamber;
    a hollow stem having a proximal end and a distal end, the proximal end of the stem being attached to the receptacle such that the stem forms a passageway extending from the chamber, the stem having a length sufficient that the stem penetrates the parietal peritoneal membrane and extends into the peritoneal cavity;
    a diametrally enlarged flange attached to the stem such that, when the conduit is implanted under a layer of skin adjacent the peritoneal cavity and the flange is secured adjacent the parietal peritoneal membrane, the distal end of the hollow stem is directed toward the mesenteric peritoneal membrane; and
    mounting means for mounting the receptacle under a layer of skin adjacent the peritoneal cavity.

11. A subcutaneously implantable injection conduit as defined in claim 10 wherein the receptacle comprises a cavity formed as an inverted, right frustoconical vessel having a diameter greater than depth with a circular base forming the open top of the chamber and connected at the apex of the frustoconical vessel to the hollow stem.

12. A subcutaneously implantable injection conduit as defined in claim 10 wherein the receptacle comprises a funnel-shaped receiver and the hollow stem is mounted to the apex of the funnel-shaped receiver.

13. A subcutaneously implantable injection conduit as defined in claim 12 wherein the apex of the funnel-shaped receiver includes a countersunk bore and the hollow stem is telescopically mounted in the bore.

14. A subcutaneously implantable injection conduit as defined in claim 13 wherein the hollow stem is fabricated from a suitable material to accommodate the hollow stem being adjustable in length.

15. A subcutaneously implantable injection conduit as defined in claim 10 wherein the diametrally enlarged flange is attached adjacent the distal end of the hollow stem, the flange thereby inhibiting the stem from retracting into tissue into which the conduit is implanted.

16. A subcutaneously implantable injection conduit as defined in claim 10 wherein the mounting means comprises a velour covering over the injection conduit, the velour accommodating tissue ingrowth.

17. A subcutaneously implantable injection conduit as defined in claim 10 wherein the penetrable membrane is fabricated with a dome configuration from a resilient material, the dome allowing the penetrable membrane to be depressed to expel the drug from the receptacle.

18. A method for injecting a drug into a peritoneal cavity in a direction toward the mesenteric peritoneal membrane, the method comprising the steps of:
obtaining an injection conduit, comprising:
a shallow vessel with an open top; a penetrable membrane covering the open top of the vessel;
a hollow stem having a proximal end and a distal end, the proximal end of the stem being attached to the vessel such that the stem forms a passageway extending from the vessel; and
a diametrally enlarged flange attached to the stem such that, when the conduit is implanted underneath a layer of skin adjacent the peritoneal cavity and the flange is secured adjacent the parietal peritoneal membrane, the distal end of the hollow stem is directed toward the mesenteric peritoneal membrane;
implanting the injection conduit underneath a layer of skin adjacent the peritoneal cavity with the membrane being generally parallel to the skin, the hollow stem penetrating the parietal peritoneal membrane and extending into the peritoneal cavity, the diametrally enlarged flange being secured adjacent the parietal peritoneal membrane, the distal end of the hollow stem being directed toward the mesenteric peritoneal membrane, and the passageway communicating between the vessel and the peritoneal cavity; and
injecting a drug into the peritoneal cavity by penetrating the layer of skin and the penetrable membrane with a hollow needle and forcing the drug through the hollow needle into the vessel with the hollow stem carrying the drug into the peritoneal cavity in a direction toward the mesenteric peritoneal membrane.

19. A method as defined in claim 18 wherein the implanting step further comprises securing the hollow stem in the peritoneal cavity thereby preventing dislodgement of the hollow stem.

20. A method as defined in claim 18 wherein the injection circuit further comprises a biocompatible velour material covering at least a portion of the injection conduit, the biocompatible velour material providing for tissue ingrowth into the velour material after implanting the injection conduit.

21. A method as defined in claim 18 wherein the vessel is fabricated from a puncture-resistant material.

22. A method as defined in claim 18 wherein the diametrally enlarged flange is attached adjacent the distal end of the stem, the flange thereby inhibiting the stem from retracting into tissue into which the injection conduit is implanted.

23. A method as defined in claim 18 wherein the penetrable membrane is fabricated from a resilient material and with a dome-like configuration, the dome extending away from the vessel.

24. A method as defined in claim 23 wherein the injecting step further comprises selectively, manually depressing the dome thereby expelling the drug from the vessel into the peritoneal cavity in a direction toward the mesenteric peritoneal membrane.

25. A method as defined in claim 24 wherein the depressing step comprises manually releasing the dome, the resilient material returning the dome to its dome-like configuration and repeating the depressing step thereby flushing the vessel.

26. A method as defined in claim 18 wherein the vessel comprises a diametrally enlarged convergent receiving surface.

27. A method as defined in claim 18 wherein the drug is insulin and wherein the insulin, upon entering the peritoneal cavity through the hollow stem so as to contact the mesenteric peritoneal membrane, is absorbed into the blood circulation of the portal venous system via said mesenteric peritoneal membrane, whereby the insulin is transported directly to the liver.

28. A peritoneal catheter comprising:
a body having a diametrally enlarged, convergent receiving surface and having an opening in the receiving surface, a periphery around the receiving surface, a raised rim circumscribing the periphery, and a shelf below the rim;
a hollow stem attached to the body, the stem forming a passageway extending from the opening; and
a diametrally enlarged, penetrable cover across the receiving surface in spaced relationship therewith, the cover being assisted by the rim in forming a receiving reservoir in combination with the receiving surface, and the cover having a lip that is engagedly received by the shelf.

29. An implantable peritoneal injection catheter, comprising:
a body having a penetration-resistant, diametrally enlarged, convergent receiving surface and an opening at the center of the receiving surface, said body comprising a circular periphery around the convergent receiving surface, a raised rim circumscribing the periphery, an annular shelf below the rim, and a bore which is countersunk into the body from the side opposite the convergent surface such that the countersunk bore is in alignment with the opening;
a diametrally enlarged, penetrable cover across the receiving surface in spaced relationship therewith, the cover being assisted by the raised rim in forming a receiving reservoir in combination with the receiving surface, the cover comprising an annular lip that is engagedly received by the shelf, and the cover being fabricated from a resilient material and having a dome-like configuration, the dome extending away from the receiving surface; and a hollow stem having a proximal end and a distal end, the proximal end of the stem being telescopically received into the countersunk bore such that the stem forms a passageway extending from the opening, the distal end of the stem being formed as a diametrally enlarged flange, and the stem having a predetermined length such that, when the catheter is implanted under a layer of skin adjacent to a peritoneal cavity, the stem extends from the body into the peritoneal cavity with the distal end of the stem being inside the peritoneal cavity and the enlarged flange residing against a wall of the peritoneal cavity so as to surround a point on the wall of the peritoneal cavity through which the stem enters the peritoneal cavity, the stem thereby accommodating fluid communication into the peritoneal cavity, and the flange inhibiting the stem from retracting into tissue into which the catheter is implanted.

30. The implantable peritoneal injection catheter defined in claim 29 wherein the cover further comprises a circumferential groove, the groove serving as a channel for receiving a suture means, the suture means securing the cover to the body.

31. The implantable peritoneal injection catheter defined in claim 29 further comprising means for mounting the catheter under a layer of skin adjacent to the peritoneal cavity, said mounting means comprising a biocompatible velour covering over at least a portion of the external surface of the peritoneal catheter, the velour covering providing for tissue ingrowth into the velour material.

32. A subcutaneously implantable injection conduit for injecting insulin into a peritoneal cavity in a direction toward the mesenteric peritoneal membrane, comprising:

an injection receiver having a penetration-resistant, diametrally enlarged, convergent receiving surface and an opening at the center of the receiving surface, said injection receiver comprising a circular periphery around the convergent receiving surface, a raised rim circumscribing the periphery, an annular shelf below the rim, and a bore which is countersunk into the injection receiver from the side opposite the convergent surface such that the countersunk bore is in alignment with the opening;

a diametrally enlarged, penetrable cover across the receiving surface in spaced relationship therewith, the cover being assisted by the raised rim in forming a receiving reservoir in combination with the receiving surface, the cover comprising an annular lip that is engagedly received by the annular shelf, and the cover being fabricated from a resilient material and having a dome-like configuration, the dome extending away from the receiving surface;

a hollow stem having a proximal end and a distal end, the proximal end of the stem being telescopically received into the countersunk bore in the injection receiver such that the stem forms a passageway extending from the opening in the receiving surface, and the stem having a length sufficient that, when the injection conduit is implanted in tissue adjacent the peritoneal cavity, the stem penetrates the parietal peritoneal membrane and extends from the injection receiver into the peritoneal cavity; and a diametrally enlarged flange attached adjacent the distal end of the hollow stem such that the flange inhibits the stem from retracting into tissue into which the conduit is implanted, and such that, when the flange is secured adjacent the parietal peritoneal membrane, the distal end of the stem is directed toward the mesenteric peritoneal membrane, whereby the insulin, upon entering the peritoneal cavity through the hollow stem, contacts the mesenteric peritoneal membrane and is absorbed into the blood circulation of the portal venous system via said mesenteric peritoneal membrane, whereby the insulin is transported directly to the liver.

33. A subcutaneously implantable injection conduit as defined in claim 32 further comprising means for mounting the conduit in tissue adjacent the peritoneal cavity, said mounting means comprising a biocompatible velour covering over at least a portion of the external surface of the conduit, the velour covering providing for tissue ingrowth into the velour material.

* * * * *

UNITED STATES PATENT AND TRADEMARK OFFICE
CERTIFICATE OF CORRECTION

PATENT NO. : 4,405,305

DATED : September 20, 1983

INVENTOR(S) : Robert L. Stephen, et al.

It is certified that error appears in the above—identified patent and that said Letters Patent is hereby corrected as shown below:

Column 5, line 34, "diabetics" should be --diabetes--

Column 10, line 33 (claim 8), "a a channel" should be --as a channel--

Column 12, line 2, (claim 20), "injection circuit" should be --injection conduit--

Signed and Sealed this

Twenty-seventh Day of December 1983

[SEAL]

Attest:

GERALD J. MOSSINGHOFF

Attesting Officer     Commissioner of Patents and Trademarks